(12) United States Patent
Yamamoto et al.

(10) Patent No.: US 8,062,454 B2
(45) Date of Patent: Nov. 22, 2011

(54) PROCESS AND APPARATUS TO ATTACH ELASTIC MEMBERS TO DISPOSABLE WEARING ARTICLE BEING CONTINUOUSLY MANUFACTURED

(75) Inventors: Hiroki Yamamoto, Kagawa-ken (JP); Akihide Ninomiya, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 2449 days.

(21) Appl. No.: 10/705,228

(22) Filed: Nov. 12, 2003

(65) Prior Publication Data
US 2006/0185135 A1    Aug. 24, 2006

(30) Foreign Application Priority Data
Nov. 12, 2002 (JP) ................. 2002-328829

(51) Int. Cl.
*B32B 15/00* (2006.01)
(52) U.S. Cl. .............. 156/229; 28/116; 28/134
(58) Field of Classification Search ........ 156/229; 28/116, 134
See application file for complete search history.

(56) References Cited

U.S. PATENT DOCUMENTS

| | | | | |
|---|---|---|---|---|
| 5,525,175 A | * | 6/1996 | Blenke et al. | 156/161 |
| 5,660,664 A | * | 8/1997 | Herrmann | 156/161 |
| 5,779,689 A | * | 7/1998 | Pfeifer et al. | 604/385.25 |
| 6,106,944 A | * | 8/2000 | Heikkila et al. | 428/397 |
| 6,123,882 A | * | 9/2000 | Uchida et al. | 264/87 |
| 6,505,791 B1 | * | 1/2003 | Syndikus et al. | 242/477.2 |
| 6,574,520 B1 | * | 6/2003 | Liu et al. | 700/96 |
| 6,895,835 B2 | * | 5/2005 | Cordeiro | 74/665 A |

FOREIGN PATENT DOCUMENTS

| | | |
|---|---|---|
| EP | 1410778 | 4/2004 |
| JP | 7-136210 | 5/1995 |
| JP | 08-132576 | 5/1996 |
| JP | 8-132576 | 5/1996 |
| JP | 11-332913 | 12/1999 |
| WO | 96/23475 | 8/1996 |

OTHER PUBLICATIONS

EP Search Report issued Sep. 22, 2008.

* cited by examiner

*Primary Examiner* — Kimberly K McClelland
(74) *Attorney, Agent, or Firm* — Lowe, Hauptman, Ham & Berner, LLP

(57) ABSTRACT

A continuous web as a component of a disposable wearing article is fed in a machine direction and first continuous elastic members are fed via guide elements adapted to oscillate the elastic members in a cross direction. Each of the guide elements has a first servomotor having a rotary shaft adapted to repeat reversal of its rotational direction, a first arm connected directly with the rotary shaft and extending in a direction crossing the rotary shaft so that the first arm swings around the rotary shaft as the rotary shaft rotates, and a first feed member adapted to direct the first continuous elastic members toward the guide element formed on the first arm.

20 Claims, 7 Drawing Sheets

PROCESS AND APPARATUS TO ATTACH ELASTIC MEMBERS TO DISPOSABLE WEARING ARTICLE BEING CONTINUOUSLY MANUFACTURED

BACKGROUND OF THE INVENTION

The present invention relates to a process and apparatus to attach elastic members to a disposable wearing article being continuously manufactured such as a disposable diaper or training pants. The present application is based on, and claims priority from, Japanese Application Serial Number 2002-328829, filed Nov. 12, 2002, the disclosure of which is hereby incorporated by reference herein in its entirety.

In the course of continuously manufacturing disposable wearing articles such as disposable diapers, it is well known to feed continuous elastic members toward a single continuous web being fed in a machine direction as a component member of the article while these continuous elastic members are oscillated in a cross direction relative to the machine direction and to attach these continuous elastic members in a stretched state to the continuous web. For example, in the case of the process and the apparatus for attachment of the elastic members to the pull-on diaper disclosed in Japanese Patent Application Publication No. 1999-332913A, guide means for positioning of the elastic members are provided so as to be opposed to the web continuously fed in the machine direction. These guide means are oscillated in the cross direction orthogonal to the machine direction by driving means including a servo mechanism.

The servo mechanism adopted by the apparatus disclosed in the above cited publication comprises a servomotor and a timing belt connecting an output shaft of the servomotor with the positioning guide means so that the positioning guide means may move along a rectilinearly extending feed means as the timing belt travels. In this well-known apparatus, a rotational velocity of the servomotor depends on various factors such as an inertia of the timing pulley mounted on the output shaft of the servomotor and rotating together with the output shaft, an inertia of the traveling belt, an inertia of the positioning guide means moving along the feed means, a vibration of the belt during its traveling and a friction between the positioning guide means and the feed means. These factors interfere with rotation of the servomotor at a high speed and consequently impede a production rate for the diaper from being improved.

SUMMARY OF THE INVENTION

It is an object of the present invention to provide a process and an apparatus for manufacturing of disposable wearing articles so improved that a motor serving to oscillate elastic members being fed toward a web which is running in a machine direction can be rotated at a desired high speed and such high rotational speed of the motor can be efficiently utilized to improve a production rate.

The object set forth above is achieved by a first aspect of the present invention relating to the process and a second aspect thereof relating to the apparatus.

According to the first aspect of the present invention, there is provided a process generally comprising steps of feeding at least a single continuous web in a machine direction as a component member of a disposable wearing article being continuously manufactured, feeding continuous elastic members toward at least one surface of the web while the continuous elastic members are oscillated in a cross direction relative to the machine direction, and attaching the continuous elastic members in a stretched state to the one surface in accordance with a desired layout.

The process according to the first aspect of the present invention comprises the steps of: feeding the web to a nip between a pair of press rolls substantially being in contact with each other and adapted to rotate in the machine direction around respective axes extending parallel to each other in the cross direction; and feeding the elastic members from upstream of the pair of press rolls to the nip between the press rolls via guide means adapted to oscillate the elastic members in the cross direction and attaching the elastic members to the web by means of an adhesive. Each of the guide means comprises: a motor having a rotary shaft extending in a direction crossing the axes and adapted to repeat reversal of its rotational direction; an arm connected directly with the rotary shaft and extending in a direction crossing the rotary shaft, the arm being formed on its distal end with guide means adapted for passage of the elastic members, and the arm being adapted to swing around the rotary shaft as the rotary shaft rotates; and at least one feed member located upstream of the rotary shaft as viewed in the machine direction and adapted to direct the elastic members toward the guide means. In the course of running from the feed member to the pair of press rolls via the guide means, the elastic members are attached to the web while the elastic members are oscillated in the cross direction by the arm connected directly with the rotary shaft so as to repeat reversal of its swinging direction.

The first aspect of the present invention relating to the process includes the following embodiments.

A servomotor is used as said motor.

The servomotor is actuated by a controller containing therein a program adapted to rotate the servomotor on the basis of a running speed of at least the web in the machine direction and the layout desired for the elastic members.

The arm is formed from a composite material comprising any one selected from the group consisting of carbon fiber, glass fiber, metallic fiber, synthetic fiber, semi-synthetic fiber and natural fiber and any one selected from the group consisting of thermoplastic synthetic resin and thermosetting synthetic resin.

The axes of the pair of press rolls extend in a horizontal direction, the rotary shaft of the motor extends in a vertical direction and the arm extends in the horizontal direction from the rotary shaft toward the nip between the pair of press rolls.

The elastic members are directed from the guide means to the nip between the pair of press rolls so that the elastic members is in coincide with a tangential line with respect to a region in which the pair of press rolls substantially contact each other.

The elastic members extend from the feed member to the guide means at a deviation angle of 10° or less relative to the horizontal direction.

According to the second aspect of the present invention relating to the apparatus, there is provided an apparatus for feeding at least single continuous web in a machine direction as a component member of a disposable wearing article being continuously manufactured, feeding continuous elastic members toward at least one surface of the web while the continuous elastic members are oscillated in a cross direction relative to the machine direction, and attaching the continuous elastic members in a stretched state to the one surface in accordance with a desired layout.

The apparatus according to the second aspect of the present invention comprises: a pair of press rolls extending in parallel to each other and substantially contacting each other, the pair of press rolls rotating in the machine direction around respective axes extending in the cross direction so as to feed the web in the machine direction, and a guide means located upstream of the pair of the press rolls as viewed in the machine direction to oscillate the elastic members in the cross direction. Each of the guide means comprises: a motor having a rotary shaft extending in a direction crossing the axes and adapted to repeat reversal of its rotational direction; an arm connected directly with the rotary shaft and extending in a direction crossing the rotary shaft, the arm being formed on its distal end with the guide means adapted for passage of the elastic members, and the arm being adapted to swing around the rotary shaft as the rotary shaft rotates; and at least one feed member located upstream of the rotary shaft as viewed in the machine direction and adapted to direction the elastic members toward the guide means.

The second aspect of the present invention relating to the apparatus includes the following embodiments.

The motor is a servomotor.

The servomotor is electrically connected with a controller containing therein a program adapted to rotate the servomotor on the basis of a running speed of at least the web in the machine direction and the layout desired for the elastic members.

The arm contains a composite material comprising any one selected from the group consisting of carbon fiber, glass fiber, metallic fiber, synthetic fiber, semi-synthetic fiber and natural fiber and any one selected from the group consisting of thermoplastic synthetic resin and thermosetting synthetic resin.

The axes of the pair of press rolls extend in a horizontal direction, the rotary shaft of the motor extends in a vertical direction and the arm extends in the horizontal direction from the rotary shaft toward the nip between the pair of press rolls.

The arm extends substantially in coincide with a tangential line with respect to a region in which the pair of press rolls substantially contact each other.

The feed member and the guide means are located so that the elastic members extend from the feed member to the guide means at a deviation angle of 10° or less relative to the horizontal direction.

DETAILED DESCRIPTION OF THE PREFERRED EMBODIMENTS

Details of process and apparatus according to the present invention to attach elastic members to the disposable wearing articles continuously manufactured will be more fully understood from the description of a disposable diaper as a typical example given hereunder with reference to the accompanying drawings.

Figure 1:
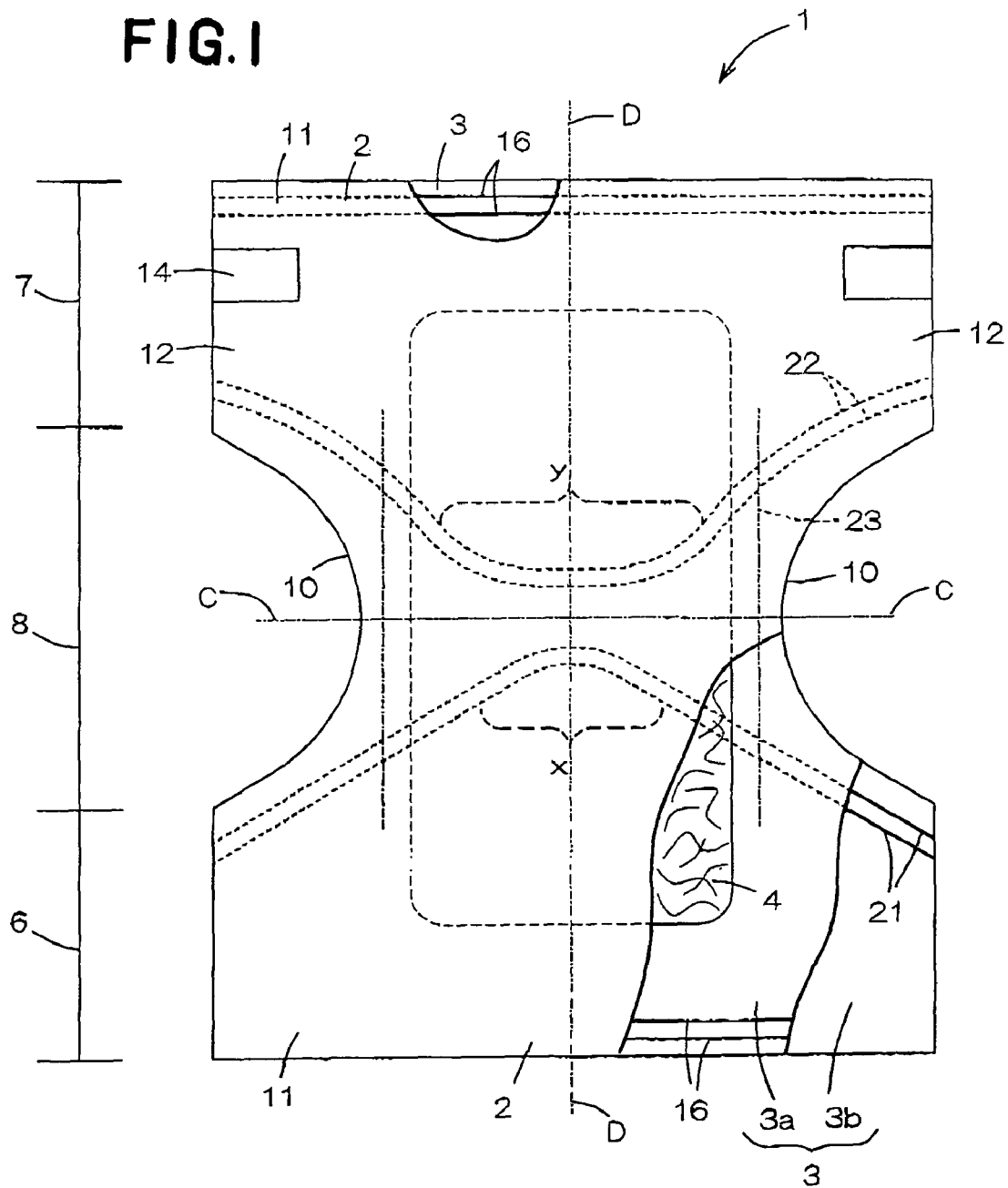
FIG. 1 is a partially cutaway plan view showing a disposable wearing article (diaper)
Figure 2:
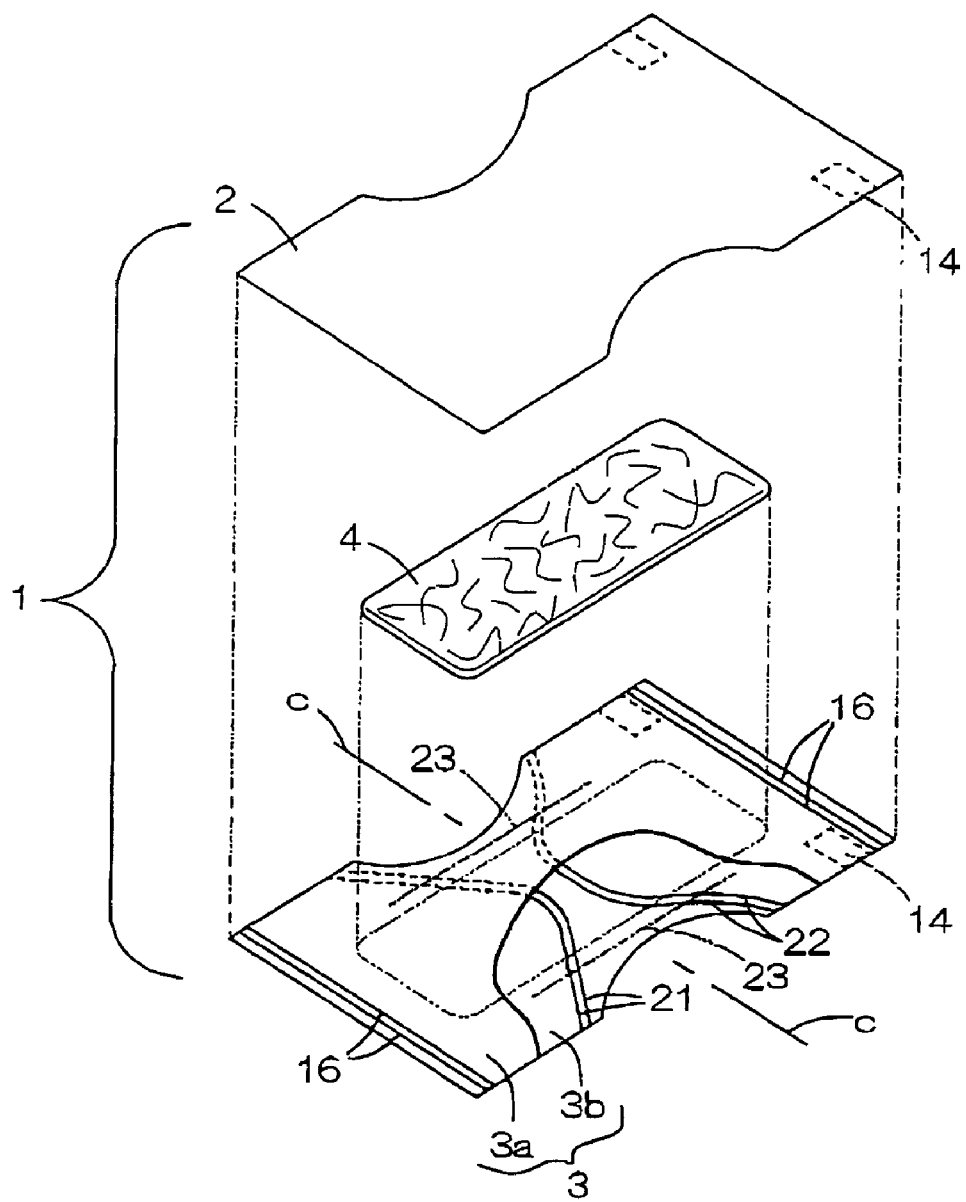
FIG. 2 is an exploded perspective view of the diaper shown in FIG. 1.

FIG. 1 is a partially cutaway plan view showing a disposable diaper 1 and FIG. 2 is an exploded perspective view of this diaper 1. The diaper 1 comprises a liquid-pervious topsheet 2, a liquid-impervious backsheet 3 and a liquid-absorbent core 4 interposed between these two sheets 2, 3. Portions of the top- and backsheets 2, 3 extending outward beyond a peripheral edge of the core 4 are overlaid and joined together by means of a hot melt adhesive (not shown) so as to form front and rear end flaps 11 and right and left side flaps 12. The backsheet 3 comprises an inner sheet 3a facing the topsheet 2 and an outer sheet 3b facing the inner sheet 3a These sheets 3a, 3b are identical to each other in shape as well as in size and joined together using an adhesive or a welding technique. The diaper 1 constructed in this manner has an hourglass-like planar shape and is composed of a front waist region 6, a rear waist region 7 and a crotch region 8 extending between these two waist regions 6, 7. In the crotch region 8, the side flaps 12 curve inwardly of the diaper 1 to define notches 10 destined to surround wearer's legs. In the rear waist region 7, the side flaps 12 include tape fasteners 14 attached thereto. The end flaps 11 in the front and rear waist regions 6, 7 respectively include waist elastic members 16 secured in a stretched state to at least one of the top- and backsheets 2, 3. In the crotch region 8 and in the vicinity thereof, a plurality of front elastic members 21 and a plurality of rear elastic members 22 are interposed between the inner and outer sheets 3a, 3b constituting the backsheet 3 and attach to the inner surface of at least one of these inner and outer sheets 3a, 3b so that these elastic members 21, 22 extend across the diaper 1 and extend along the respective leg surrounding notches 10, describing curves which are convex toward a center line C-C bisecting a longitudinal dimension of the diaper 1. The front and rear elastic members 21, 22 are at least partially in a stretched state. A line D-D extending in a vertical direction as viewed in FIG. 1 is a center line bisecting a transverse dimension of the diaper 1 about which the diaper 1 is symmetric.

In the diaper 1 constructed in the manner as has been described above, the front elastic members 21 cooperate with the rear elastic members 22 to make peripheries of the leg surrounding notches 10 elastically stretchable and contractible. The elastic members 21, 22 may be curved in an appropriate pattern or laid closer one to another or laid to cross one another in order to ensure that the respective notches 10 can smoothly expand or contract. It is also possible to attach additional elastic members in a stretched state to an inner surface of the topsheet 2 or to an inner surface of the backsheet 3 in the vicinity of the notches 10 along imaginary lines 23 extending in the vertical direction as viewed in FIG. 1 so that one or more elastic members are associated with each of these imaginary lines 23 and laid to cross the front and rear elastic members 21, 22. The topsheet 2 of the diaper 1 may be formed by nonwoven fabric or perforated plastic film. The inner sheet 3a, one component of the backsheet 3, may be formed by liquid-impervious or breathable and liquid-impervious plastic film or nonwoven fabric and the outer sheet 3b, the other component of the backsheet 3, may be formed by breathable nonwoven fabric. The inner sheet 3a serves to make the backsheet 3 liquid-impervious and the outer sheet 3b serves to provide the backsheet 3 with cloth-like touch. It is possible without departing from the scope of the present invention to replace such backsheet 3 by a backsheet comprising the inner sheet 3a alone or by a backsheet comprising the outer sheet 3b alone.

Figure 3:
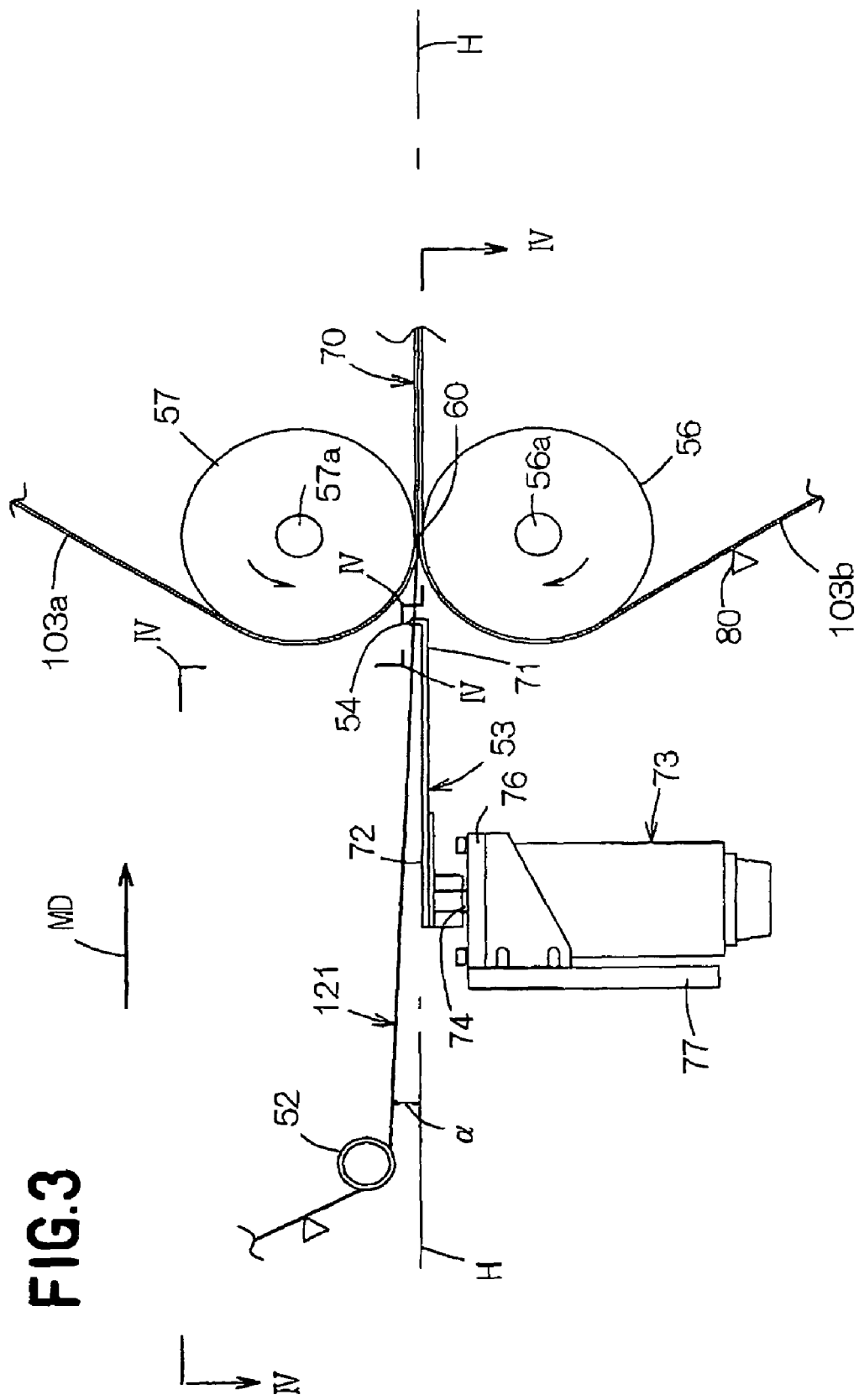
FIG. 3 is a side view schematically showing a part of a process to make the diaper shown in FIG. 1.
Figure 4:
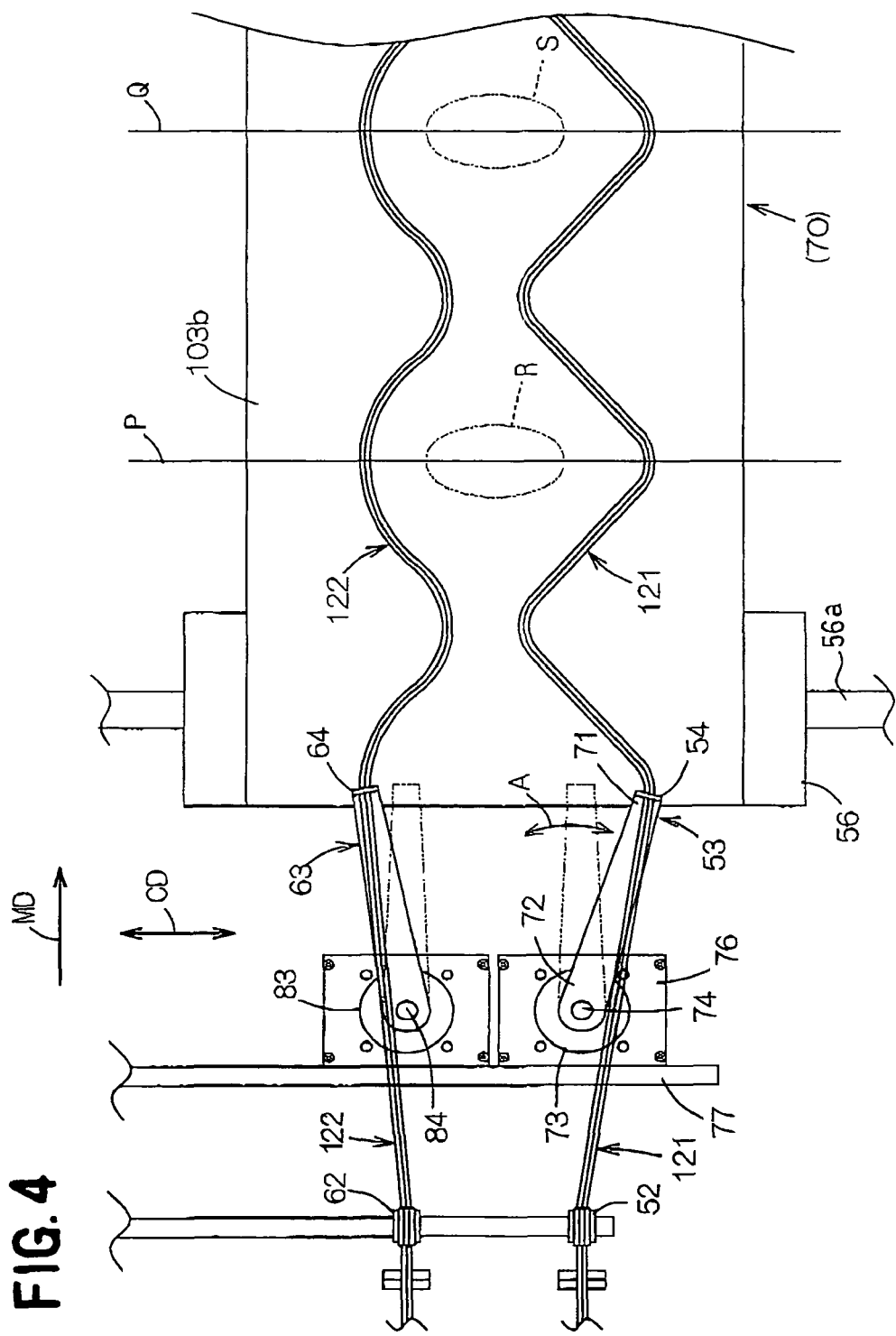
FIG. 4 is an overhead view showing the part of the process in a direction indicated by arrows IV-IV in FIG. 3.

FIG. 3 is a side view showing an apparatus used in the step of a serial process for continuous manufacturing of the diaper 1 in which first and second continuous elastic members 121, 122 destined to become the front and rear elastic members 21, 22, respectively, are attached to first and second continuous webs 103a, 103b destined to become the inner and outer sheets 3a, 3b of the backsheet 3, respectively, and FIG. 4 is an overhead view showing this apparatus in a direction indicated by arrows IV-IV in FIG. 3. In this step, the first and second continuous elastic members 121, 122 are fed in a machine direction MD from the left hand toward the right hand as viewed in FIG. 3. The first and second continuous webs 103a, 103b are fed from above and below as viewed in FIG. 3, respectively, and driven in the machine direction MD.

The first continuous elastic members 121 are directed by a first feed roll 52 to first guide means 54 of a first arm 53. Having passed through the first guide means 54, the first continuous elastic members 121 run to a contact line 60 between lower and upper press rolls 56, 57 having respective axes 56a, 57a extending parallel to each other. These lower and upper press rolls 56, 57 are paired to form so-called nip rolls adapted to rotate in the machine direction MD around the respective axes 56a, 57a extending in a cross direction CD orthogonal to the machine direction MD, preferably in a horizontal plane. The contact line 60 between these paired press rolls 56, 57 refers to a region in which the lower press roll 56 and the upper press roll 57 come closest to each other in the vertical direction as viewed in FIG. 3. In this region, the press rolls 56, 57 cooperate with each other to press the first and second continuous elastic members 121, 122 against the first and second continuous webs 103a, 103b and, in other words, these press rolls 56, 57 are substantially in contact with each other through the intermediary of these members 121, 122 and webs 103a, 103b. The contact line 60 in FIG. 3 extends in the cross direction CD parallel to the axes 56a, 57a of the lower and upper press rolls 56, 57 as viewed in FIG. 4.

As will be apparent from FIG. 4, the second continuous elastic members 122 are directed by a second feed roll 62 to second guide means 64 of a second arm 63. Having passed through the second guide means 64, the second continuous elastic members 122 run to the contact line 60 between lower and upper press rolls 56, 57.

The second continuous web 103b is coated by a coater 80 with a hot melt adhesive (not shown) and then directed to the lower press roll 56 while the first continuous web 103a is directed from above to the upper press roll 57 as viewed in FIG. 3.

The first and second continuous elastic members 121, 122 and the first and second continuous webs 103a, 103b run together on the contact line 60 between the lower and upper press rolls 56, 57 so that the elastic members 121, 122 may be sandwiched between the webs 103a, 103b. These members and webs are integrated together by means of a hot melt adhesive coated on the web 103b to form a continuous composite web 70. According to the illustrated embodiment, the composite web 70 runs as a stock material for the backsheet 3 in the machine direction MD substantially in the horizontal plane H. In order to integrate these members 121, 122 and the webs 103a, 103b together, it is possible without departing from the scope of the invention to coat, in addition to or instead of the web 103b, the members 121, 122 or the web 103a with a hot melt adhesive.

In the apparatus, the first arm 53 has a distal end 71 formed with the guide means 54 and a proximal end 72 opposed to the distal end 71 and directly connected with a rotary shaft 74 of a first servomotor 73. The first arm 53 extends toward the contact line 60 in a direction intersecting the rotary shaft 74, preferably in the horizontal plane H. The first servomotor 73 is mounted on a base plate 77 by means of a bracket 76 so that the position of the servomotor 73 in the cross direction DC may be freely adjusted. The rotary shaft 74 of the first servomotor 73 extends in a direction intersecting the direction in which the respective axes 56a, 57a of the lower and upper press rolls 56, 57 extend, preferably, in the horizontal plane. The direction in which the rotary shaft 74 rotates can be repeatedly reversed at high frequency. The first art 53 directly connected with the rotary shaft 74 is adapted to swing to and fro around the rotary shaft 74 in a direction indicated by a double-headed arrow A at the same angular velocity as that of the rotary shaft 74 so that the swinging direction can be repeatedly reversed at high frequency. Such to and fro swing of the first arm 53 causes the first continuous elastic members 121 to oscillate in the cross direction CD as they pass through the first guide means 54 and thereby continuously changes the position of these elastic members 121 in the cross direction CD on the contact line 60 on which the lower and upper press rolls 56, 57 substantially contact each other. As the position is continuously changed in this manner, the first continuous elastic members 121 are still continuous in the machine direction and undulate in the cross direction CD so that the first continuous elastic members 121 may be attached in accordance with a desired layout to the first and second continuous webs 103a, 103b. It should be understood that the first continuous elastic members 121 are shown in FIG. 4 as attached to the second continuous elastic members 103b.

The first continuous elastic members 121 run in a previously stretched state from the first feed roll 52 to the first guide means 54. The to and fro swing of the first arm 53 causes the first elastic members 121 are further stretched at a desired percentage in the vicinity of the contact line 60 as they are squeezed between the lower and upper press rolls 56, 57. Having been attached to the first and second continuous webs 103a, 103b, desired stretching ratios are achieved in respective regions of the first continuous elastic members 121 in the longitudinal direction.

The first arm 53 is directly connected with the rotary shaft 74 of the first servomotor 73 actuated by a controller containing therein a program adapted to provide the first continuous elastic members 121 with a desired stretching ratio and a desired layout depending on a running speed of the first continuous web 103a and/or the second continuous web 103b. The first arm 53 actuated in this manner must be sufficiently lightweight and stiff to follow the reversal of swinging direction quickly repeated by the first servomotor 73, in other words, to eliminate the anxiety that the presence of the first arm 53 might affect the frequency at which the reversal of swinging direction should be repeated. The preferred first arm 53 is made of composite comprising any one selected from the group consisting of synthetic fiber such as carbon fiber or polyamide fiber known in trade name of Kevlar, metallic fiber such as titanium fiber, glass fiber, semi-synthetic fiber and natural fiber and any one selected from the group consisting of thermoplastic synthetic resin and thermosetting synthetic resin. The first arm 53 made of composite comprising carbon fiber and thermosetting synthetic resin is one embodiment of particularly preferred embodiments. With this embodiment, it has been experimentally found that a full weight of the first arm 53 inclusive of the proximal end 72 can be reduced to 96 to 121 g and rotation of the first servomotor 73 to which the first arm 53 is directly connected can be repeatedly reversed at the maximum angular acceleration as high as 15,000 rad/sec$^2$ by using a carbon composite having a specific gravity of 1.5 to 1.8 and a bending modulus of 98 to 201 GPa to form the first arm 53 having a full length of 250 to 350 mm. In this experiment, the first arm 53 has been directly connected with the rotary shaft 74 of the first servomotor 73 in a manner that the first arm 53 defines a substantial tangent line with respect to the contact line 60 between the lower and upper press rolls 56, 57 and practically lies in the horizontal plane H which is orthogonal to the axes 56a, 57a of the rolls 56, 57. Further-more, the first feed roll 52 and the first guide means 54 have been positioned so that the first continuous elastic members 121 can travel substantially in the horizontal plane H from the first feed roll 52 to the contact line 60 between the lower and upper press rolls 56, 57 via the first guide means 54 and a deviation angle α of the first continuous elastic members 121 relative to the horizontal plane H can be maintained within a range of 0 to 10° in the course defined between the first feed roll 52 and the first guide means 54.

Referring again to FIGS. 3 and 4, the second continuous elastic members 122 follows the substantially same process flow as that for the first continuous elastic members 121 until they are attached to the first and second continuous webs 103a, 103b by means of a hot melt adhesive (not shown). Specifically, the second continuous elastic members 122 is directed by the second feed roll 62 to second guide means 64 of the second arm 63. Having passed through the second guide means 64, the second continuous elastic members 122 run to the contact line 60 between the lower and upper press rolls 56, 57. The second arm 63 is directly connected with the rotary shaft 84 of the second servomotor 83 actuated by a controller (not shown) containing therein a program adapted to control the to and fro swing of the second arm 63 so that the second continuous elastic members 122 may be attached to the second continuous web 103b in accordance with a desired layout as well as at a desired stretching ratio depending on a running speed of the attached continuous web 103b running in the machine direction MD. Having been attached to the first and second continuous webs 103a, 103b, desired stretching ratios are achieved in respective regions of the second continuous elastic members 122 in the longitudinal direction. In the illustrated embodiment, the second continuous elastic members 122 are distinguished from the first continuous elastic members 121 in that the program actuating the second servomotor 83 differs from the program actuating the first servomotor 73 and, in consequence, the layout and the stretching ratio on the second continuous web 103b are different from those exhibited by the first continuous elastic members 121. Obviously, it is possible to actuate the first and second servomotors 73, 83 by one and same program so that the first and second continuous elastic members 121, 122 may be provided with the layout and the stretching ratio common to both of these first and second continuous elastic members 121, 122. While the second servomotor 83 is illustrated to be mounted on the base plate 77 like the case of the first servomotor 73, it is possible to mount the second servomotor 83 on a base plate provided separately of the base plate 77. The second servomotor 83 may be either same as or different from the first servomotor 73. The length of the second arm 63 may be either same as nor different from the length of the first arm 53. The lengths of these first and second arms 53, 63 may be appropriately adjusted depending on a particular attachment layout required for the first and second continuous elastic members 121, 122.

Figure 5:
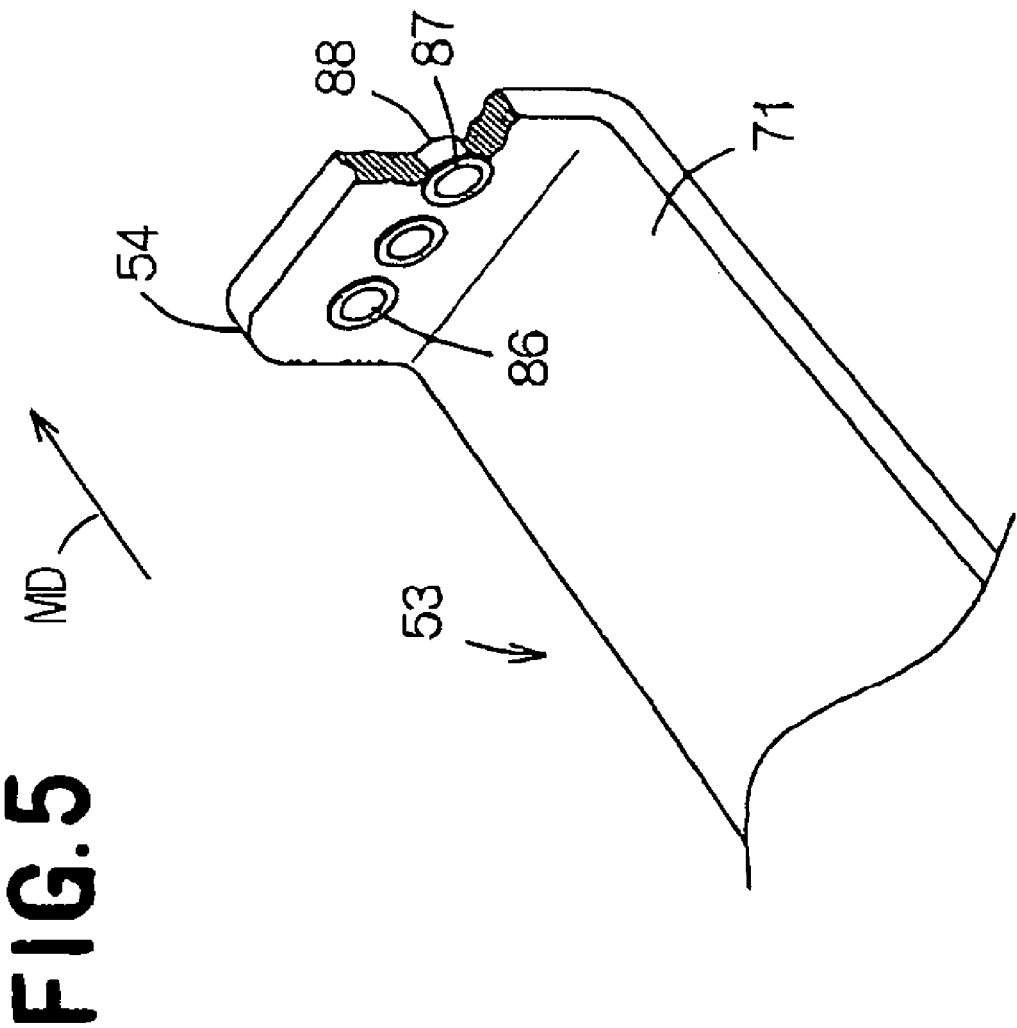
FIG. 5 is a partial perspective view of a first arm.

FIG. 5 is a partially cutaway perspective view showing the first arm 53. The distal end 71 of the first arm 53 is formed with the first guide means 54 which is formed, in turn, with a plurality of through-holes 86 adapted for insertion of the individual one of the elastic members 121. These through-holes 86 are formed by tubular members 88 each having a flange 87 serving to prevent the tubular member 88 from falling off in the machine direction MD. The members 88 are preferably made of ceramics to eliminate an anxiety that the members 88 might resist the first continuous elastic members 121 running at a high speed in the machine direction MD and thereby abrade the members 121 as they more or less frictionally pass through these tubular members 88. The guide means 64 of the second arm 63 may be formed in the same manner as the guide means 54 of the first arm 53. In the first guide means 54, the through-holes 86 may be replaced by the other structures, for example, U-shaped grooves so far as such alternative structures are suitable for guiding of the first continuous elastic members 121.

Referring to FIG. 4, straight lines P, Q extending in the cross direction CD and circular imaginary lines R, S intersection these straight lines P, Q, respectively, indicate the lines along which the composite web 70 of FIG. 3 are to be cut and cut off, respectively. It should be noted that, in FIG. 4, the cutting lines and the cut off regions are indicated not on the composite web 70 but on the second continuous web 103b. The composite web 70 may be cut along the lines P, Q, R, S to obtain the individual backsheets 3 shown in FIG. 1.

Figure 6:
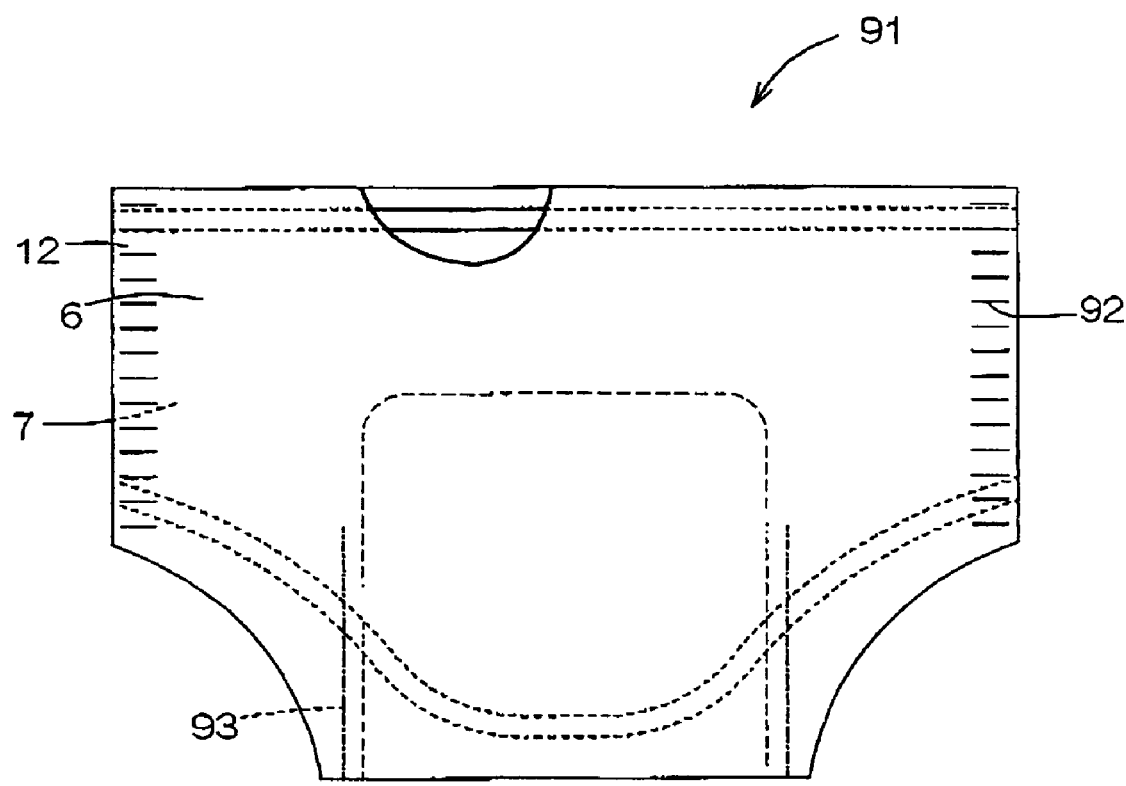
FIG. 6 is a partially cutaway plan view showing a disposable pants-type diaper.

FIG. 6 is a partially cutaway plan view showing a pull-on disposable diaper 91. This diaper 91 is obtained by removing the tape fasteners 14 from the diaper 1 of FIG. 1 manufactured using the continuous composite web 70, placing the front and rear waist regions 6, 7 upon each other with the topsheet 2 inside and connecting the waist regions 6, 7 along the respective flaps 12 of the waist regions 6, 7 using an adhesive or a heat-sealing technique in joining areas 92 arranged intermittently in a vertical direction as viewed in FIG. 6. Imaginary lines 93 correspond to the imaginary lines 23 in FIG. 1 and suggest positions at which the leg elastic members are to be laid and are to be supplemented, if desired. Such diaper 91 is useful also as a diaper for incontinent patients or training pants for infants.

Figure 7:
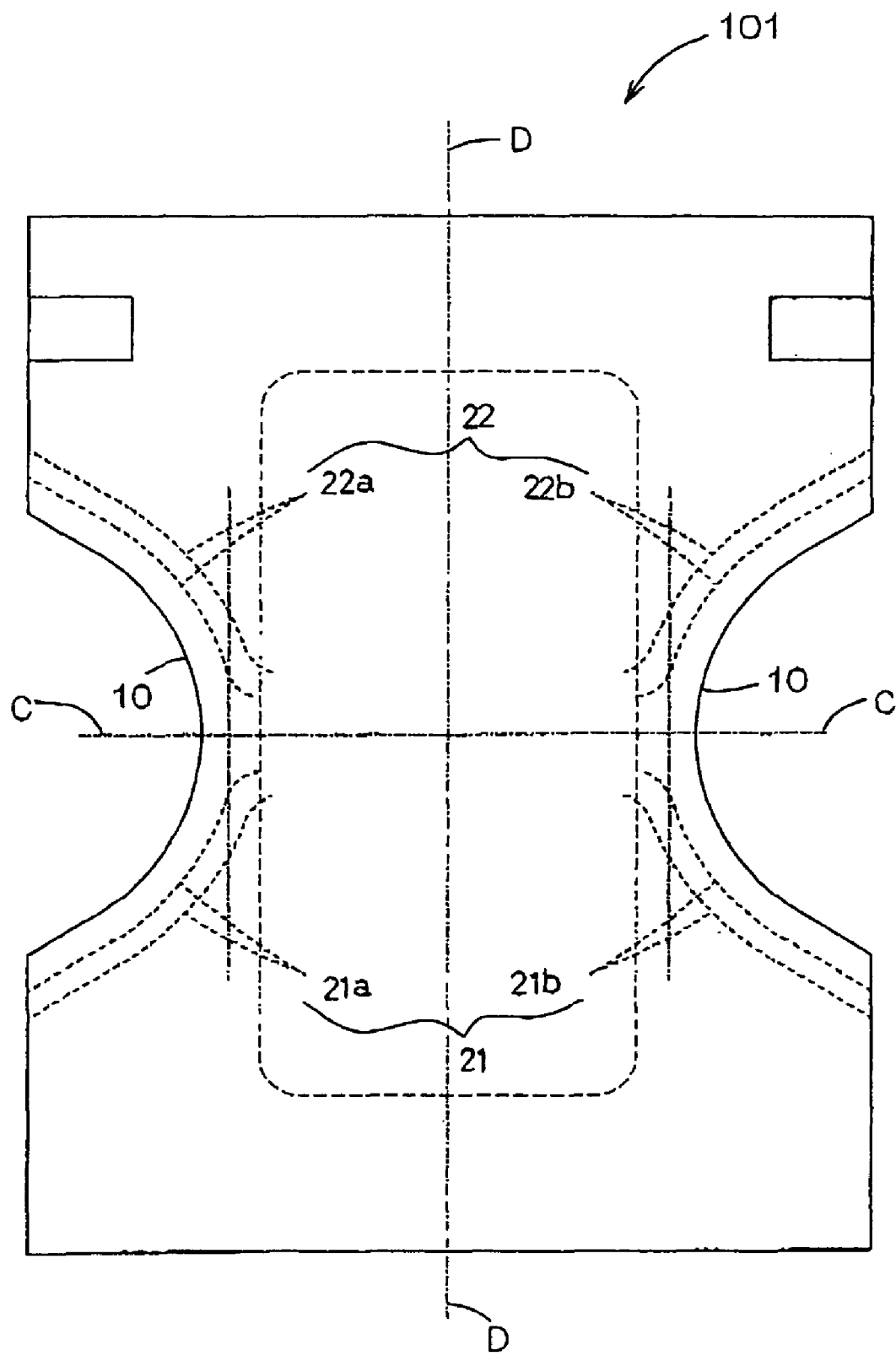
FIG. 7 is a plan view showing a disposable diaper implemented in a manner different from that shown in FIG. 1.

FIG. 7 is a view similar to FIG. 1 showing a disposable diaper 101 according to another embodiment. In this diaper 101, the front and rear elastic members 21, 22 in the diaper 1 of FIG. 1 have been cut at intersecting points of these members 21, 22 and the longitudinal center line D-D and portions x, y of the elastic members 21, 22 have contracted to the vicinity of the leg surrounding notches 10. The front elastic members 21 in the diaper 101 are divided into sections 21a and sections 21b while the rear elastic members 22 of the diaper 101 are divided into sections 22a and section 22b. In the step illustrated in FIG. 4, the front elastic members 21 and the rear elastic members 22 are attached to the second continuous web 103b only in the vicinity of the regions destined to form the leg surrounding notches 10 and cut in any subsequent step into sections 21a, 21b, 22a, 22b.

The diaper 1 of FIG. 1 provided by the present invention has the backsheet 3 which may be formed by only the liquid-impervious inner sheet 3a and, in such diaper 1, the front elastic members 21 and the rear elastic members 22 are joined to the inner surface of the inner sheet 3a. Alternatively, the backsheet 3 may be formed by the inner sheet 3a having the front elastic members 21 and the rear elastic members 22 attached to the outer surface thereof and the outer sheet 3b joined to the outer surface of the inner sheet 3a. To obtain such backsheet 3, not the second continuous web 103b but the first continuous web 103a are fed from below to the lower press roll 56 and no web is fed to the upper press roll 57 or the second continuous web 103b is previously joined to the lower surface of the first continuous web 103a fed from below in the step illustrated in FIGS. 3 and 4.

It is possible without departing from the scope of the invention to arrange a plurality of sets each comprising the servomotor and the arm directly connected with the rotary shaft of the servomotor intermittently in the machine direction MD and thereby to bond the continuous elastic members to both surfaces of the continuous web traveling in the machine direction MD. By arranging a plurality of sets each comprising the servomotor and the arm in this manner, it is possible to cross the continuous elastic members 121 with the second continuous elastic members 122 on the second continuous web 103b. When these sets each comprising the servomotor and the arm intermittently in the machine direction MD, a pair of press rolls will be arranged behind each of these sets in the machine direction MD.

The present invention is applicable not only to the disposable wearing article illustrated as specific embodiments but also to the other disposable wearing article such as a disposable gown used in medical site or a sporting disposable wearing article.

The process and the apparatus according to the present invention is primarily characterized in that the continuous elastic members are fed through the arms each directly connected with the rotary shaft of the associated servomotor having the rotational direction adapted to be repeatedly reversed at high frequency so that the continuous elastic members may undulate in the cross direction relative to the machine direction and be attached to the continuous web running in the machine direction in the undulated pattern. Such arrangement allows the arms to swing to and fro at a high frequency, in other words, such arrangement allows an output of the wearing article per unit time to be improved. The arms are made from a carbon composite or the like and are sufficiently stiff and lightweight to ensure that the to and fro swing of the arms can be stabilized even when the rotational direction of the servomotors are repeatedly reversed at high frequency. By connecting the arms directly with the rotary shafts of the respective servomotors, driving means such as pulleys and belts which have usually been essential of the well known art can be eliminated and consequently troubles due to abrasion and/or damage of the parts.

What is claimed is:

1. A process, comprising the steps of:
feeding at least a single continuous web in a machine direction as a component member of a disposable wearing article being continuously manufactured,
feeding continuous elastic members toward at least one surface of said web while said continuous elastic members are oscillated in a cross direction relative to said machine direction, and
attaching said continuous elastic members in a stretched state to said one surface in accordance with a desired layout,
wherein
in the step of feeding said web, the web is fed to a nip between a pair of press rolls substantially being in contact with each other and rotate in said machine direction around respective axes extending parallel to each other in said cross direction;
in the step of feeding said elastic members, the elastic members are fed from upstream of said pair of press rolls to the nip between said press rolls via at least one guiding mechanism that oscillates said elastic members in said cross direction, and
in the step of attaching said elastic members to said web, the elastic members are attached to said web by means of an adhesive;
wherein each of said at least one guiding mechanism comprises:
a motor having a rotary shaft extending in a direction crossing said axes and adapted to repeat reversal of its rotational direction;
an arm connected directly with said rotary shaft and extending in a direction crossing said rotary shaft, said arm being formed on its distal end with a guiding element adapted for passage of said elastic members, and said arm being adapted to swing around said rotary shaft as said rotary shaft rotates, wherein said arm is formed from a composite material comprising carbon fiber and any one selected from the group consisting of thermoplastic synthetic resin and thermosetting synthetic resin, and has a specific gravity of 1.5 to 1.8 and a bending modulus of 98 to 201 GPa; and
at least one feed member located upstream of said rotary shaft as viewed in said machine direction and adapted to direct said elastic members toward said guiding element; and
wherein, in the course of running from said feed member to said pair of press rolls via said at least one guiding mechanism, said elastic members are attached to said web while said elastic members are oscillated, at a maximum angular acceleration of 15,000 rad/sec$^2$, in said cross direction by said arm connected directly with said rotary shaft so as to repeat reversal of its swinging direction;
said process further comprising arranging said axes of said press rolls horizontally, said rotary shaft of said motor vertically, and said arm to extend horizontally from said rotary shaft toward said nip between said press rolls.

2. The process according to claim 1, further comprising using a servomotor as said motor.

3. The process according to claim 2, further comprising controlling said servomotor on the basis of a running speed of at least said web in said machine direction and said layout desired for said elastic members.

4. The process according to claim 1, wherein said elastic members are directed from said guiding element to said nip between said pair of press rolls so that said elastic members are positioned in a plane tangential to said press rolls in a region in which said press rolls substantially contact each other.

5. The process according to claim 1, wherein said elastic members extend from said feed member to said guiding element at a deviation angle of 10° or less relative to a horizontal plane.

6. The process according to claim 1, further comprising maintaining an axis of said rotary shaft stationary relative to the axes of said press rolls while the elastic members are being fed and oscillated at the same time towards said nip.

7. The process according to claim 1, wherein said elastic members are attached to said web by means of the adhesive only in regions corresponding to leg openings of the disposable wearing article being manufactured;
said method further comprising
cutting the elastic members between said regions so that the cut elastic members do not extend across en entire width of the disposable wearing article being manufactured, and
attaching an absorbent core to said web, wherein portions of the cut elastic members that have not been attached to said web contract to a relaxed state and are located near transverse edges of the absorbent core.

8. The process according to claim 1, further comprising controlling rotational oscillating movements of the arm of each said at least one guiding mechanism such that a stretching ratio of the elastic members fed by one guiding mechanism is different from that of the elastic members fed by the other guiding mechanism.

9. The process according to claim 1, wherein said arm has a full weight of 96 to 121 g, and a full length of 250 to 350 mm.

10. The process according to claim 9, further comprising maintaining an axis of said rotary shaft stationary relative to the axes of said press rolls while the elastic members are being fed and oscillated at the same time towards said nip.

11. The process according to claim 1, wherein said composite material comprises said carbon fiber and said thermosetting synthetic resin.

12. An apparatus for feeding at least a continuous web in a machine direction as a component member of disposable wearing articles being continuously manufactured, feeding at least one continuous elastic member toward at least one surface of said web while said at least one continuous elastic member is oscillated in a cross direction transverse to said machine direction, and attaching said at least one continuous elastic member in a stretched state to said one surface in accordance with a desired layout, said apparatus comprising:

a pair of press rolls substantially contacting each other, said press rolls being rotatable around respective axes extending in said cross direction so as to feed said web in said machine direction, and a guiding mechanism located upstream of said press rolls as viewed in said machine direction to oscillate said at least one elastic member in said cross direction;

wherein said guiding mechanism comprises:

a motor which has a rotary shaft extending in a direction transverse to said axes and is adapted to repeatedly reverse a rotational direction of said rotary shaft;

an arm connected directly with said rotary shaft and longitudinally extending in a direction transverse to said rotary shaft, said arm being formed on a distal end thereof with a guiding element through which said at least one elastic member is passable, and said arm being adapted to swing around said rotary shaft as said rotary shaft rotates; and at least one feed member located upstream of said rotary shaft as viewed in said machine direction and adapted to direct said at least one elastic member toward said guiding element;

wherein an axis of said rotary shaft is stationary relative to the axes of said press rolls; and wherein said arm is formed from a composite material comprising carbon fiber and any one selected from the group consisting of thermoplastic synthetic resin and thermosetting synthetic resin, and has a specific gravity of 1.5 to 1.8 and a bending modulus of 98 to 201 GPa, thereby allowing the servomotor to repeatedly swing said arm at an angular acceleration of up to 15,000 rad/sec$^2$.

13. The apparatus according to claim 12, wherein said motor is a servomotor.

14. The apparatus according to claim 13, further comprising a controller, wherein said servomotor is electrically connected with the controller which is programmed to rotate said servomotor on the basis of a running speed of at least said web in said machine direction and said layout desired for said at least one elastic member.

15. The apparatus according to claim 12, wherein said axes of said press rolls extend horizontally, said rotary shaft of said motor extends vertically, and said arm extends horizontally from said rotary shaft toward a nip between said press rolls.

16. The apparatus according to claim 12, wherein said arm extends substantially in a plane tangential to said press rolls in a region in which said press rolls substantially contact each other.

17. The apparatus according to claim 12, wherein said feed member and said guiding element are located so that said at least one elastic member extends from said feed member to said guiding element at a deviation angle of 10° or less relative to a horizontal plane parallel to the axes of said press rolls.

18. The apparatus according to claim 12, wherein a rotational axis about which the arm swings coincides with the axis of said rotary shaft.

19. The apparatus according to claim 12, wherein said arm has a full weight of 96 to 121 g, and a full length of 250 to 350 mm.

20. The apparatus according to claim 12, wherein said composite material comprises said carbon fiber and said thermosetting synthetic resin.

* * * * *